United States Patent
Guralnik et al.

(10) Patent No.: US 9,433,661 B2
(45) Date of Patent: Sep. 6, 2016

(54) INSULIN-CONTAINING INFANT FORMULA

(71) Applicant: NUTRINIA LTD., Nazareth Illit (IL)

(72) Inventors: Mario Guralnik, Irvine, CA (US);
Naim Shehadeh, Kfar-Yasif (IL);
Michal Olshansky, Tel Aviv (IL)

(73) Assignee: NUTRINIA LTD., Nazareth Illit (IL)

( * ) Notice: Subject to any disclaimer, the term of this patent is extended or adjusted under 35 U.S.C. 154(b) by 0 days.

(21) Appl. No.: 14/872,460

(22) Filed: Oct. 1, 2015

(65) Prior Publication Data
US 2016/0022782 A1    Jan. 28, 2016

Related U.S. Application Data

(63) Continuation of application No. 14/404,057, filed as application No. PCT/IL2013/050463 on May 30, 2013, now abandoned.

(60) Provisional application No. 61/653,669, filed on May 31, 2012.

(51) Int. Cl.
| | | |
|---|---|---|
| *A23L 1/29* | (2006.01) | |
| *A61K 38/28* | (2006.01) | |
| *A23L 1/305* | (2006.01) | |
| *A61K 47/36* | (2006.01) | |

(52) U.S. Cl.
CPC ............... *A61K 38/28* (2013.01); *A23L 1/296* (2013.01); *A23L 1/3053* (2013.01); *A61K 47/36* (2013.01); *A23V 2002/00* (2013.01)

(58) Field of Classification Search
CPC ............................. A23L 1/296; A61K 38/28
See application file for complete search history.

(56) References Cited

U.S. PATENT DOCUMENTS

| | | |
|---|---|---|
| 6,365,177 B1 | 4/2002 | Shahadeh |
| 6,399,090 B1 | 6/2002 | Shehadeh |
| 2006/0147494 A1 | 7/2006 | Barzilay |
| 2007/0248652 A1 | 10/2007 | Barzilay |

FOREIGN PATENT DOCUMENTS

| | | |
|---|---|---|
| WO | 9962558 A1 | 12/1999 |
| WO | 2004112494 A2 | 12/2004 |
| WO | 2005115473 A2 | 12/2005 |
| WO | 2012052060 A1 | 4/2012 |

OTHER PUBLICATIONS

The American Academy of Pediatrics "Breastfeeding and the use of Human Milk" Pediatrics. 129: e827-e841 (Feb. 2012).
Buts, Jean-Paul et al "Oral Insulin is Biologically Active on Rat Immature Enterocytes" Journal of Pediatric Gastroenterology & Nutrition. 25:2: 230-232 (Aug. 1997).
A.N. Corps et al "Stimulation of intestinal epithelial cell proliferation in culture by growth factors in human and ruminant mammary secretions" Journal of Endocrinology. 113: 285-290 (Nov. 1987).
Agostoni, Carlo et al "Breast-feeding: A Commentary by the ESPGHAN Committee on Nutrition" Journal of Pediatric Gastroenterology and Nutrition. 49: 112-125 (Jan. 2009).
Kinouchi, Toshi et al "Milk-Borne Insulin With Trypsin Inhibitor in Milk Induces Pancreatic Amylase Development at the Onset of Weaning in Rats" Journal of Pediatric Gastroenterology and Nutrition. 30:5:515-521 (May 2000).
Larkin, Marilynn "Out with the jab, in with painless pills" The Lancet. 349: 1676 (Jun. 1997).
Schatz, Desmond A. "Prevention of insulin-dependent diabetes mellitus: an overview of three trails" Cleveland Clinic Jouranl of Medicine 63: 5: 270-274 (Sep. 1996).
Health and Consumer Protection Directorate-General "Report of the Scientific Committee on Food on the Revision of Essential Requirements of Infant Formulae and Follow- on Formulae" Scientific Committee on Food. 1-211 (May 2003).
Shehadeh N, et al "Insulin in human milk and the prevention of type 1 diabetes" Pediatric Dabaetes. 2: 175-177 (Jul. 2001).
Shehadeh N. et al "Importance of insulin content in infant diet: suggestion for a new infant formula" Acta Paediatr. 90:93- 95 ISSN: 0803-5253 (2001).
Shehadeh N. et al "Insulin in human milk: postpartum changes and effect of gestational age" Arch Dis Child Fetal Neonatal Ed 88: F214-F216 (Aug. 2003).
Robert J. Shulman "Oral Insulin Increases Small Intestinal Mass and Disaccharidase Activity in the Newborn Miniature Pig" Pediatric Research 38:2: 171-175 (Apr. 1990).
R. J. Shulman "Effect of enteral administration of insulin on intestinal development and feeding tolerance in preterm infants: a pilot study" Arch Dis Child Fetal Neonatal Ed. 86: F131-F133 (Nov. 2002).
T. J. Whitmore "Analysis of Insulin in Human Breast Milk in Mothers with Type 1 and Type 2 Diabetes Mellitus" International Journal of Endocrinology 296368 :1-9 (2012).
Shamir, R. et al. "Insulin in human milk and the use of hormones in infant formulas", The importance of immunonutrition, vol. 77, pp. 57-64, 2013.

*Primary Examiner* — Gina Justice
(74) *Attorney, Agent, or Firm* — Browdy and Neimark, PLLC

(57) ABSTRACT

The present invention provides compositions methods and kits for improved infant formula, particularly to insulin-supplements and formulae comprising same that mimic the diurnal rhythm and/or the postpartum variation of insulin in human milk.

20 Claims, 6 Drawing Sheets

INSULIN-CONTAINING INFANT FORMULA

FIELD OF THE INVENTION

The present invention relates to methods and kits for improved infant formula, particularly to insulin-supplements and formulae comprising same that mimic the diurnal rhythm and/or the postpartum variation of insulin concentration in human milk.

BACKGROUND OF THE INVENTION

Breastfeeding is acknowledged as the natural and advisable way of supporting the healthy growth and development of infants due to its nutritional and immunological advantages (ESPGHAN Committee on Nutrition: Agostoni C. et al. Breast-feeding: A commentary by the ESPGHAN Committee on Nutrition. J Pediatr Gastroenterol Nutr 2009. 49:112-25). Breast milk provides the most suitable diet for infant's nutritional requirements. It also provides the infant with immune protection against a wide range of infection related diseases (Shulman R. J. Pediatr Res 1990. 28:171-5), and is found to provide long-term benefits in the area of certain cognitive developments. The benefits of breastfeeding are widely recognized by physicians groups including the American Academy of Pediatrics (AAP), which recommends that infants be exclusively breastfed for the first six months of life (American Academy of Pediatrics, *Pediatrics*, 112:e827-e841, 2012). The AAP further describes the benefits of exclusive breastfeeding as including decreased incidence of infection, gastroenteritis, obesity, and diabetes. It is also well known that the composition of human milk changes over the first few weeks following delivery of an infant. Human milk is referred to as colostrum during the first 5 days after birth, transition milk during days 6-14 after birth, and mature milk thereafter. During each stage of lactation, the corresponding human milk composition differs considerably. Colostrum and transition milk, for example, have lower caloric densities than mature milk, as well as higher protein and lower carbohydrate concentrations. Vitamin and minerals as well as hormone concentrations also vary in the three defined human milk groups. However, in the last few decades, breast-feeding has declined in all the technologically advanced societies of the world and also, even to a lesser extent, in developing countries. Many women choose not to nurse their babies at all or cease nursing after a short period of time. Others are prevented from nursing due to various medical reasons, including women suffering from certain transmissible or non-transmissible diseases, a specific example being women carrying HIV. Women that gave birth to premature babies or term babies that did not survive are also prevented from nursing.

There are many different infant nutritional formulas that are commercially available or otherwise known in the infant formula art. These infant formulae comprise a range of nutrients to meet the nutritional needs of the growing infant, and typically include lipids, carbohydrates, protein, vitamins, minerals, and other nutrients helpful for optimal infant growth and development. While an effort is made to make the commercial infant formulae similar in composition to mature human milk, they are not identical, typically due to the formula processing conditions. One of the components missing from commercial infant formulae is insulin, known to be present in its active form in maternal milk.

Observations on lactating dams and suckling rats have shown that mammalian milk insulin is biologically active, and that immature enterocytes have an increased responsiveness to the insulin (Buts J. P. et al., J Pediatr Gastroenterol Nutr 1997. 25:230-2). Insulin stimulates intestinal epithelial cell proliferation, and ileal lactase activity is increased when porcine insulin is added to feed administered to newborn piglets (Shehadeh N. et al., Pediatr Diabetes 2001. 2:175-177; Corps A. N. and Brown K. D. J Endocrinol 1987. 113:285-90). Furthermore, milk-borne insulin affects the maturation of the pancreas and induces pancreatic amylase development in rats (Kinouchi T. et al., JPGN 2000. 30:515-521). It has been previously shown that human milk insulin concentration is significantly higher (60.23±41.05 µU/ml) compared to cows' milk (16.32±5.98 µU/ml) and that insulin is hardly detected in infant formulas. The range of insulin values in human maternal milk taken 3 to 30 days after delivery was found to be between 6.45 to 305.65 µU/ml (Shehadeh N et al. 2001. Acta Paediatr 90:93-95). In additional study, it has been further evaluated whether human insulin concentration in breast milk is affected by gestational age or postnatal age. The breast milk was analyzed for insulin levels on day 3 and 10 post partum. Human milk insulin (HMI) concentration, on either day 3 or 10 post partum, was not influenced by gestational age at delivery as well as maternal age, ethnic origin, mode of delivery, weight gain in pregnancy or maternal body mass index (BMI) (Shehadeh N et al. 2003. Arch Dis Child Fetal Neonatal Ed 88:F214-F216). Insulin levels in human breast milk in mothers with type 1 and type 2 diabetes mellitus have also been studied (Whitmore T J et al. 2012 Int J Endocrinol. 2012: Article ID 296368).

Enteral insulin administration may be of benefit in reducing feeding intolerance in preterm infants (Shulman R J. Arch Dis Child Fetal Neonatal Ed. 2002. 86:F131-F133), and can suppress the development of autoimmune diabetes in mice (Schatz D. A. et al., Cleve Clin J Med 1996. 63:270-4). Orally administered insulin is usually not absorbed in the gut (Larkin M. Lancet 1997. 349:1676), and the observed effects may be local and limited to the suckling period (Shehadeh N. et al., 2001, ibid). Yet, oral insulin supplementation in non-suckling mice increases insulin serum levels and has a favorable effect on serum lipid levels, suggesting a systemic effect for insulin taken orally in this population. This is in agreement with observations in adult rats, of a transcellular (but not paracellular) intestinal transport of insulin.

While no observations were made regarding long term negative effects of oral insulin, administration of oral insulin to preterm infants from 4 to 28 days of age at a concentration as high as 4 U/kg/day, increased lactase activity and may be of benefit in reducing feeding intolerance without inducing hypoglycaemia or other adverse effects (Shulman 2002, ibid). Analyzing the effect of administered insulin on mucosal mass parameters and on expression of brush border membrane (BBM) hydrolases in a suckling rat model of immature intestine also demonstrated the safety of oral insulin given in the pharmacological range of ~10 times higher than the estimated daily intake of milk-borne insulin demonstrating the safety of oral insulin supplementation (Buts J P et al., 1997. J Pediatr Gastroenterol Nutr 25:230-2). Furthermore, this study demonstrated that insulin is able to enhance intestinal BBM enzymes prematurely especially when given in its appropriate vehicle (rat milk).

U.S. Pat. Nos. 6,365,177 and 6,399,090 disclose an infant formula in a powder or solution form comprising nutritional components and an insulin supplement. The insulin concentration is in the range of 10 to 1000 µU/ml solution (particularly 30-100 µU/ml solution) or 83-7,500 µU/grams of powder (particularly 250-750 µU/grams of powder), and when fed to an infant the chance of the infant to develop diabetes is reduced.

U.S. Applications Publication Nos. 20070248652 and 20060147494 disclose methods for encapsulation of active ingredients, including insulin, and formulations comprising same used to enhance the health status and growth performance of human and non-human organisms.

WO 2012/052060 discloses a method for increasing the growth velocity of a human infant, particularly underweight or preterm human infants, by the enteral administration of recombinant human bile-salt-stimulated lipase (rhBSSL).

There is unmet need for infant formulae which mimics the diurnal rhythm and/or postpartum change of natural human milk, and therefore provides higher similarity to the natural components of human milk.

SUMMARY OF THE INVENTION

The present invention provides methods and kits for insulin supplementation of infant formula that mimic the diurnal rhythm and/or the postpartum variation of insulin concentration in natural human milk, and reproduce the levels of insulin found in human milk. According to some aspects the present invention provides a kit comprising a plurality of infant formula portions to be used at specified times of the day or night and/or specified time after birth. According to some aspects, the insulin is premixed with the basic infant formula. According to other aspects the insulin and the basic infant formula are provided as separate components to be mixed prior to use.

The present invention discloses for the first time that insulin levels in normal human milk fluctuate during the time of day. The present invention further shows that the insulin levels in normal human milk vary during the course of several weeks postpartum. The present invention is based on these findings regarding natural human milk and provides methods systems and kits to improve infant formula by mimicking the fluctuations in insulin supplementation over the course of days (1-30) or months (2-3) postpartum.

According to one aspect, the present invention provides a kit for insulin-supplemented infant formula, comprising a plurality of portions of infant formula, wherein each portion comprises insulin, wherein the concentration of the insulin in each of the plurality of portions mimics the concentration of insulin in human milk at a given day and time of day postpartum, wherein the day is between day 1 to day 30 postpartum, wherein the time of day is selected from 6 AM to 12 PM, 12 PM to 6 PM, and 6 PM to 12 AM; and instructions for feeding an infant with the insulin-supplemented infant formula. According to some embodiments, the concentration of insulin in each portion of formula corresponds to the concentration range of insulin indicated at a given day and time of day in Table 1. According to other embodiments, the concentration of insulin in each portion of formula corresponds to the mean concentration of insulin indicated at a given day and time of day in Table 1. The insulin concentration in the plurality of portions of insulin can be the same or different.

According to another aspect, the present invention provides a kit for insulin-supplemented infant formula, comprising a plurality of portions of infant formula, a plurality of portions of insulin; and instructions for how to mix the insulin with the formula such that the insulin concentration in the formula mimics the concentration of insulin in human milk at a given day and time of day postpartum, wherein the day is between day 1 to day 30 postpartum, wherein the time of day is selected from 6 AM to 12 PM, 12 PM to 6 PM and 6 PM to 12 AM. According to some embodiments, the concentration of insulin in each insulin portion corresponds to the concentration range of insulin indicated at a given day and time of day in Table 1. According to other embodiments, the concentration of insulin in each insulin portion corresponds to the mean concentration of insulin indicated at a given day and time of day in Table 1. The insulin concentration in the plurality of insulin portions can be the same or different.

According to another aspect, the present invention provides a kit for insulin-supplemented infant formula, comprising a plurality of portions of infant formula, wherein each portion comprises insulin, wherein the concentration of the insulin mimics the concentration of insulin in human milk at a given day and time of day postpartum, wherein the day is between day 30 to day 84 postpartum, wherein the time of day is selected from 6 AM to 12 PM, 12 PM to 6 PM and 6 PM to 12 AM; and instructions for feeding an infant with the insulin-supplemented infant formula. According to some embodiments, the concentration of insulin in each portion of formula corresponds to the concentration range of insulin indicated at a given day and time of day in Table 1. According to other embodiments, the concentration of insulin in each portion of formula corresponds to the mean concentration of insulin indicated at a given day and time of day in Table 1. The insulin concentration in the plurality of portions of infant formula can be the same or different.

According to another aspect, the present invention provides a kit for insulin-supplemented infant formula, comprising a plurality of portions of infant formula, wherein each portion comprises insulin, wherein the concentration of the insulin mimics the concentration of insulin in human milk at a given day and time of day postpartum, wherein the day is between day 1 to day 30 postpartum, wherein the time of day is selected from 6 AM to 6 PM and 6 PM to 12 AM; and instructions for feeding an infant with the insulin-supplemented infant formula. According to some embodiments the concentration of insulin in each portion of formula corresponds to the mean concentration of insulin indicated at a given day and time of day in Table 2. The insulin concentration in the plurality of portions of infant formula can be the same or different.

According to certain embodiments, the concentration of insulin in each portion of the formula is selected from (i) a concentration that is 10% higher than the mean concentration of the insulin measured between 6 AM to 6 PM at a given day postpartum and (ii) a concentration that is 10% lower than the average concentration of the insulin measured between 6 PM to 12 AM at a given day postpartum.

According to certain embodiments, the concentration of insulin in each portion of formula is selected from (i) a concentration that is 10% higher than the mean concentration of the insulin indicated for 6 AM to 6 PM of a given day in Table 2 and (ii) a concentration that is 10% lower than the average concentration of the insulin indicated for 6 PM to 12 AM of a given day in Table 2.

According to additional aspect, the present invention provides a kit for insulin-supplemented infant formula, comprising a plurality of portions of infant formula, wherein each portion comprises insulin, wherein the concentration of the insulin in each of the plurality of portions mimics the average concentration of insulin in human milk at a given time period postpartum, wherein the time period postpartum is selected from day 0-5, 6-15, 16-30, 31-60, 61-90; and instructions for feeding an infant with the insulin-supplemented infant formula. According to some embodiment, the kit comprises plurality portions of infant formula comprising different insulin concentrations. According to other embodiments, at least two of the formula portions comprise the same concentration of insulin.

According to another aspect, the present invention provides a kit for insulin-supplemented infant formula, comprising a plurality of portions of infant formula, a plurality of portions of insulin; and instructions for how to mix the insulin with the formula such that the insulin concentration in the formula mimics the concentration of insulin in human milk at a given time period postpartum, wherein the time period postpartum is selected from day 0-5, 6-15, 16-30, 31-60, 61-90. According to some embodiment, the kit comprises plurality portions of insulin comprising different insulin concentrations. According to other embodiments, at least two of the insulin portions comprise the same concentration of insulin.

According to certain typical embodiments, the insulin is encapsulated in an encapsulating material. Encapsulating materials are typically selected from the group consisting of polysaccharides, milk powder, whey proteins, lipids, gum Arabic and microcrystalline cellulose. Other encapsulation materials well known in the art are also encompassed within the scope of the present invention.

According to one embodiment, insulin is microencapsulated within a matrix of maltodextrin (MD) to form an insulin supplement. According to other embodiment, the matrix further comprises anti oxidant, typically vitamin C. This matrix provides the encapsulated insulin with a long term stability and resistance to exposure to high temperatures (above 42° C.) in terms of preserved activity.

According to certain typical embodiments, the insulin is biologically active. According to certain embodiments, the insulin is mammalian insulin selected from the group consisting of human insulin and bovine insulin. According to certain typical embodiments, the insulin is human insulin. According these embodiments, the insulin is recombinant or semi-synthetic human insulin.

Any infant formula as is known in the art can be used as a basal formula for producing the insulin-enriched formula. Typically, the infant formula is in a form of dry powder reinstated into water to form a liquid formula prior to use. According to some embodiments, the formula is presented in a form selected from the group consisting of: dry powder for reconstitution with water, liquid concentrate for reconstitution with water and liquid ready-to-feed formula.

According to certain embodiments, the insulin is provided as an additive dry powder at a specific concentration to be mixed with the formula. According to typical embodiments, the insulin is provided as liquid additive at a specific concentration to be mixed with the formula.

According to another aspect, the invention provides a method for feeding an infant with portions of insulin-supplemented infant formula, comprising feeding the infant with a formula portion at a certain day and time of day postpartum, wherein the day is between day 1 to day 30 postpartum, wherein the time of day is selected from 6 AM to 12 PM, 12 PM to 6 PM, and 6 PM to 12 AM, and wherein each formula portion comprises insulin at a concentration that mimics the insulin concentration in human milk at the same day and time of day postpartum. According to some embodiments, the concentration of insulin in the formula corresponds to the concentration range of insulin indicated at a given day and time of day in Table 1. According to other embodiments, the concentration of insulin in the formula corresponds to the average concentration of insulin indicated at a given day and time of day in Table 1.

According to another aspect, the invention provides a method for feeding an infant with portions of insulin-supplemented infant formula, comprising feeding the infant with a formula portion at a certain day and time of day postpartum, wherein the day is between day 30 to day 84 postpartum, wherein the time of day is selected from 6 AM to 12 PM, 12 PM to 6 PM, and 6 PM to 12 AM, and, wherein each formula portion comprises insulin at a concentration that mimics the insulin concentration in human milk at the same day and time of day postpartum. According to some embodiments, the concentration of insulin in the formula corresponds to the concentration range of insulin indicated at a given day and time of day on Table 1. According to other embodiments, the concentration of insulin in the formula corresponds to the average concentration of insulin indicated at a given day and time of day in Table 1.

According to another aspect, the invention provides a method for feeding an infant with portions of insulin-supplemented infant formula, comprising feeding the infant with a formula portion at a certain day and time of day postpartum, wherein the day is between day 1 to day 30 postpartum, wherein the time of day is selected from 6 AM to 6 PM and 6 PM to 12 AM, and, wherein each formula portion comprises insulin at a concentration that mimics the insulin concentration in human milk at the same day and time of day postpartum. According to some embodiments, the concentration of insulin in the formula corresponds to the mean concentration of insulin indicated at a given day and time of day in Table 2.

According to other embodiments, the concentration of insulin in each portion of the formula is selected from (i) a concentration that is 10% higher than the mean concentration of the insulin measured between 6 AM to 6 PM at a given day postpartum, and (ii) a concentration that is 10% lower than the average concentration of the insulin measured between 6 PM to 12 AM at a given day postpartum. According to further embodiments, the concentration of insulin in each portion of formula is selected from (i) a concentration that is 10% higher than the mean concentration of the insulin indicated for 6 AM to 6 PM of a given day in Table 2, and (ii) a concentration that is 10% lower than the average concentration of the insulin indicated for 6 PM to 12 AM of a given day in Table 2.

According to another aspect, the invention provides a method for feeding an infant with portions of insulin-supplemented infant formula, comprising feeding the infant with a formula portion during a given time period postpartum, wherein the time period postpartum is selected from day 0-5, 6-15, 16-30, 31-60, 61-90, wherein each formula portion comprises insulin at a concentration that mimics the average concentration of insulin in human milk at the same time period postpartum. According to certain embodiments, the plurality of insulin portions comprises at least two portions with the same insulin concentration. According to some embodiments, the plurality of insulin portions comprises different insulin concentration The methods of the present invention are directed to newborn infants during the initial weeks or months of life, typically during at least the first month of life, or during at least the first two months of life, and including up to about 3 months, up to 4 months, up to 5 month and up to 6 months of life or more.

Other objects, features and advantages of the present invention will become clear from the following description and drawings.

BRIEF DESCRIPTION OF THE FIGURES

FIG. 3A shows the plot of samples taken in the morning, FIG. 3C shows the plot of samples taken in the afternoon, and FIG. 3B shows the plot of samples taken in the evening.

DETAILED DESCRIPTION OF THE INVENTION

Figure 1:
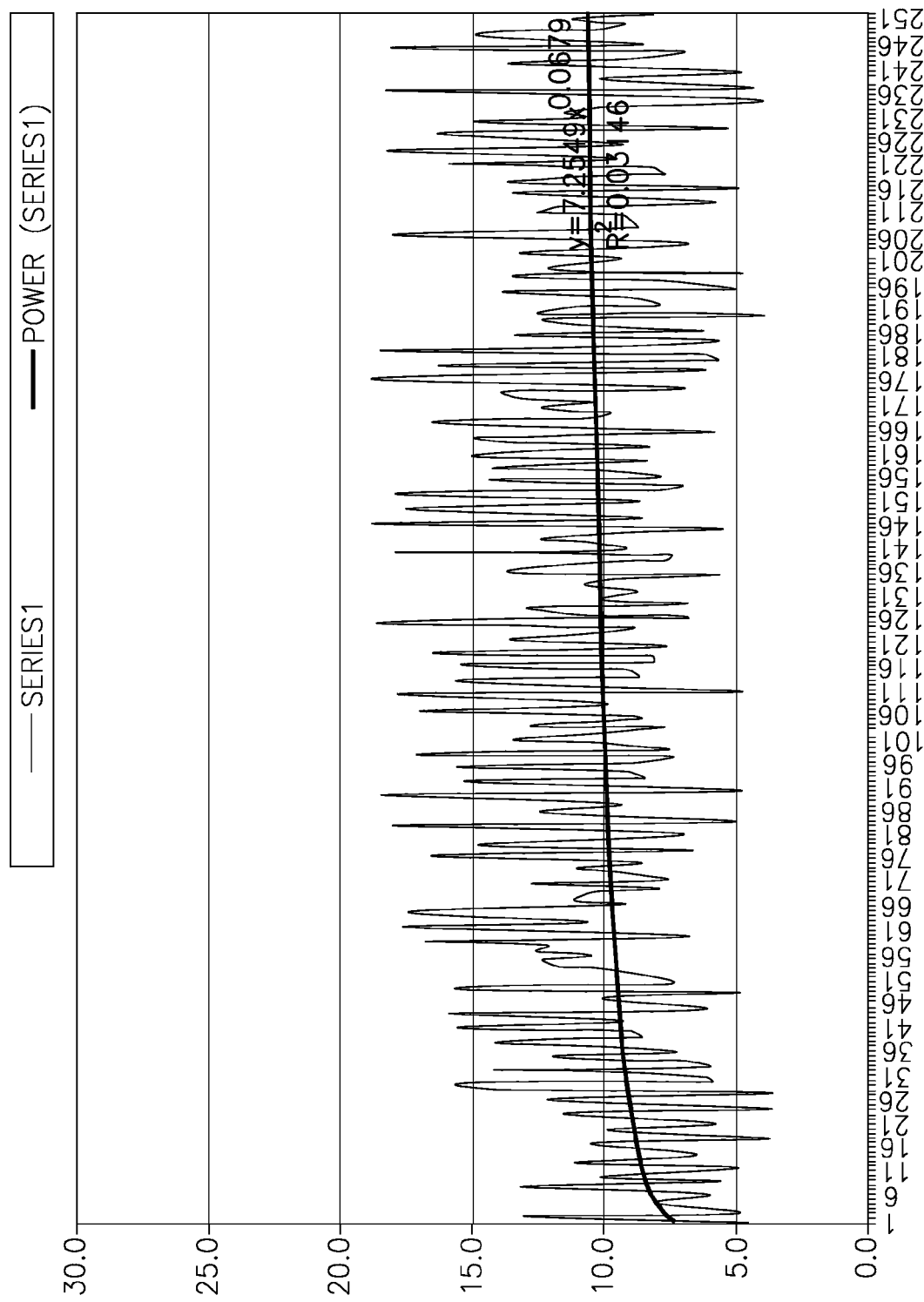
FIG. 1 shows the average insulin concentration in HM samples collected three times a day from day 1 to day 84 postpartum.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting, and technical terms are used according to conventional usage.

The present invention discloses for the first time that insulin concentration in human milk fluctuates. Observation of reproducible fluctuations in HM insulin concentration allows for the production of infant formula (IF) that can provide an infant with insulin at defined concentrations to enhance mimicking of the concentration of insulin that would be provided to the infant in HM.

ABBREVIATIONS

HM Human milk
IF Infant formula
RTF Ready to feed

The present invention discloses for the first time that endogenous insulin concentration in HM fluctuates for at least 30 days postpartum. It was observed that the concentration of insulin in a pregnant woman fluctuates throughout the peripartum period, and that these fluctuations correlate with hormonal stages in the days prior to full-term labor and delivery of the fetus. The observed insulin fluctuations in healthy pregnant women occur consistently between healthy subjects prior to, during, and after labor; and continue for at least 30 days postpartum. These postpartum fluctuations are mirrored by corresponding fluctuations of insulin in HM, and until a plateau of insulin concentration at 26-30 days postpartum.

Infant formula (IF) lacks multiple components of HM, including maternal antibodies and insulin. Inclusion of insulin in IF formulations was previously suggested for example in U.S. Pat. Nos. 6,365,177 and 6,399,090, but prior to the current disclosure, the suggested concentrations of insulin for inclusion in IF bore no relation to the natural insulin component provided to a baby at a given neonatal or postnatal time period.

The observation of reproducible fluctuations in HM insulin concentration allows for the production of IF that can provide an infant with insulin at defined concentrations to mimic the concentration of insulin that would be provided to the infant in HM.

The present invention discloses an additional outcome of insulin administration, and for the first time administration in fluctuation manner to infants. It is now shown that giving the infant a formula mimicking breast colostrum and/or milk in terms of fluctuated insulin concentrations benefits the ability to interchange infant formula and human milk feeding to an infant while maintaining a similar insulin exposure throughout.

Additionally described herein are methods of feeding an infant with the disclosed IF so that the concentration of insulin provided mimics that found in HM at the postpartum time of feeding, particularly as shown in Table 1. Current IF formulations lack an insulin component that corresponds to the actual insulin concentrations of HM on a given postpartum day.

DEFINITIONS

As used herein, the term "control" refers to a reference standard. A control can be a known value indicative of insulin concentrations in either non-pregnant women or those who have not recently given birth (within 90 days). In particular examples a control sample is taken from a subject that is known not to have a disease or condition, such as diabetes. A difference between a test sample and a control can be an increase or conversely a decrease. The difference can be a qualitative difference or a quantitative difference, for example a statistically significant difference. In other examples a control can be the amount of insulin present in commercially-available IF.

As used herein, the term "determining expression of a gene product" refers to detection of a level of expression (for example a protein or nucleic acid) in either a qualitative or a quantitative manner. In one example, it is the detection of insulin in a mother or in HM.

As used herein, the term "polypeptide" refers to any chain of amino acids, regardless of length or post-translational modification (such as glycosylation, methylation, ubiquitination, phosphorylation, or the like). "Post-translational modification" is the chemical modification of a polypeptide after its translation, for example by mono-ubiquitination, glycosylation, methylation, phosphorylation, or the like.

As used herein, the term "insulin" refers to a peptide or polypeptide hormone, which is naturally secreted by the islets of Langerhans and functions in the regulation of the metabolism of carbohydrates and fats, particularly the conversion of glucose to glycogen. The insulin may be native insulin (purified or synthetic or recombinant) or analogs thereof. According to certain embodiments, the term insulin refers to mammalian insulin. According to certain typical embodiments, the term insulin refers to recombinant human insulin and to analogs thereof, which is biologically active.

As used herein, the term "IU" (International Unit) refers to the biological equivalent of about 45.5 µg pure crystalline insulin (exactly 1/22 mg). The collection of the experimental data and its analysis and therefore the evaluations of the insulin concentration levels were obtained based on the population pharmacokinetics (population PK) approach. Hence, the experimental data and the terms and values of the present specification should be considered accordingly.

As used herein, the term "ELISA" refers to enzyme-linked immunosorbent assay (or EIA). Numerous ELISA methods and applications are known in the art, and are described in many references (See, e.g., Crowther, "Enzyme-Linked Immunosorbent Assay (ELISA)," in Molecular Biomethods Handbook, Rapley et al. [eds.], pp. 595-617, Humana Press, Inc., Totowa, N.J. [1998]; Harlow and Lane (eds.), Antibodies: A Laboratory Manual, Cold Spring Harbor Laboratory Press [1988]; Ausubel et al. (eds.), Current Protocols in Molecular Biology, Ch. 11, John Wiley & Sons, Inc., New York [1994]). In addition, there are numerous commercially available ELISA test systems.

As used herein, the term "range" with regard to insulin concentration or amount in human milk refers to all values between the low and high range concentration appearing in Tables 1 and 2 herein, with a deviation of ±10% of the specified concentrations.

As used herein, the term "increased risk" refers to an increase in the statistical probability of developing a condition relative to the general population. For example, risk factors such as a family history of diabetes or obesity can increase the risk of a subject developing diabetes or obesity.

As used herein, the term "infant formula" refers to manufactured food for feeding newborn infants and babies, particularly from birth to 12 months of age. IF is designed to replicate many of the constituent components of human milk (HM) by containing sources of protein, fat, carbohydrates and vitamins. Multiple formulations of IF are commercially available, which provide variations in the provided nutritional components. For example, in particular examples, the protein source is provided by whey separated from cow's milk. In other examples, the protein source is a soy-based protein. In still other examples the protein source is a manufactured mixture of amino acids designed for infants who are allergic to other protein sources. Examples of commercially available IF include ENFAMIL® and SIMILAC® IF, though many more brand and generic IF varieties are available.

As used herein, the term "ready-to-feed", unless otherwise specified, refers to nutritional formulas in liquid form, suitable for administration without further dilution, including ready-to-feed manufactured liquids.

As used herein, the term "isolated" refers to biological component (such as a nucleic acid, protein, cell (or plurality of cells) that has been substantially separated or purified away from other biological components of the organism in which the component naturally occurs, for example other tissues, cells, other chromosomal and extra-chromosomal DNA and RNA, proteins and organelles. Nucleic acids and proteins that have been "isolated" include nucleic acids and proteins purified by standard purification methods. The term also embraces nucleic acids and proteins, such as insulin, prepared by recombinant expression in a host cell as well as chemically synthesized nucleic acids.

As used herein, the term "neonatal" refers to the initial period of an infant's life, extending through the first four weeks, or 28 days after birth. The term "neonatal" baby is used synonymously with the term "newborn" infant or "newborn" baby.

As used herein, the term "postnatal" refers to after birth, as directed towards the baby. The postnatal period typically extends through the first six weeks after birth. As used herein, the term "postnatal" includes any specified time period (e.g. day, week or month) after birth. For example, 90 days postnatal is a 90 day-old baby.

As used herein, the term "postpartum" refers to after birth, as directed towards the mother. The postpartum period typically extends through the first six weeks after birth. As used herein, the term "postpartum" includes any specified time period (e.g. day, week or month) after birth. For example, 90 days postpartum is 90 days after a mother gives birth to a baby.

As used herein, the term "purified" refers to the term purified does not require absolute purity; rather, it is intended as a relative term. Thus, for example, a purified peptide preparation, such as insulin, is one in which the peptide or protein is more enriched than the peptide or protein is in its natural environment within a cell. In one embodiment, a preparation is purified such that the protein or peptide represents at least 50% of the total peptide or protein content of the preparation.

As used herein, the term "preterm birth" refers to a birth prior to 37 weeks gestation; can be used synonymously with "premature birth."

As used herein, the term "risk factor" refers to a factor that can increase the statistical likelihood of developing a condition, such as diabetes or obesity. Examples of risk factors for diabetes include a family history diabetes.

As used herein, the term "sample" encompasses a sample obtained from a subject, whether unfixed, frozen, or fixed in formalin or paraffin. As used herein, samples include all clinical samples useful for detection of insulin in subjects or HM, including, but not limited to, cells, tissues, and bodily fluids.

As used herein, the term "subject" refers to living multicellular vertebrate organisms, category that includes both human and veterinary subjects, including human and non-human mammals.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example." In addition, all the materials, methods, and examples are illustrative and not intended to be limiting.

Infant Formula to Mimic Fluctuations in Human Milk Insulin

According to certain embodiments, the insulin is mammalian insulin selected from the group consisting of human insulin and bovine insulin. According to certain typical embodiments, the insulin is human insulin. According these embodiments, the insulin is recombinant or semi-synthetic human insulin.

IF is well-known in the art. Multiple IF varieties are widely-available, and are suitable for use in the IF formulations described herein. The IF formulations described herein can contain all or part of the ingredients found in common and/or commercially available IF, with the addition of insulin to a final defined concentration to mimic the insulin concentration found in HM during a given postpartum time period.

In certain embodiments, the insulin-supplemented IF described herein can be provided as an IF composition pre-mixed with supplemented insulin. In certain embodiments, IF is provided as a dry powder that may be reconstituted with water. In other embodiments, the IF is supplied as a liquid concentrate for reconstitution with water. In other embodiments, the IF is in a liquid ready-to-feed (RTF) formula. Regardless of formulation type (concentrated, RTF, or dry powder), the final concentration, at feeding, of added insulin in the IF will be the same for the specified day and time period. Table 1 (see below) gives ranges and average insulin amounts for HM at a given postpartum day given time during each day (morning, 6 AM-12 PM; afternoon, 12 PM-6 PM; and evening, 6 PM-12 AM). The concentrations of insulin indicated in Table 1 can be used as a guide for the amount of insulin to be added to IF at a given day and a given time point.

For example, in particular embodiments, the IF is in a liquid ready-to-feed (RTF) formula. In some embodiments the RTF IF is supplemented with insulin at 10-15 µU/ml, and can be used to mimic the natural insulin component of HM from in the afternoon (12 PM-6 PM) at day 1 postpartum. In other embodiments the RTF IF is supplemented with insulin at 8-12 µU/ml, and can be used to mimic the natural insulin component of HM in the morning (6 AM-12 PM) at day 4 postpartum. In still other embodiments, the RTF IF is supplemented with insulin at 8-11 µU/ml, and can be used to mimic the natural insulin component of HM in the evening (6 PM-12 AM) at day 29 postpartum.

In other embodiments, the insulin supplement is provided as an additive that can be mixed at a specified concentration with any available IF known in the art. The concentration of insulin added in the IF for feeding at a given time of day and given day postpartum is designed to mimic the natural insulin component in HM, for example as is indicated in Table 1. Each of the IF and insulin can be in the form of dry powder, liquid or a liquid concentrate. In particular examples, the insulin supplement is provided as a dry powder that is mixed at a specified concentration with dry or liquid (concentrated or RTF) IF, with or without water reconstitution. In other examples, the insulin supplement is provided in a liquid to be mixed at a specified concentration with dry IF upon reconstitution, or with liquid (concentrated or RTF) IF.

Regardless of whether the supplemented insulin is provided pre-mixed with IF or as an additive to be combined with commercially-available IF, the final insulin concentrations provided are designed to mimic insulin concentrations in HM during a given time frame and on a given postpartum day, for example as indicated in Table 1.

The IF described herein is supplemented with any type of human insulin (i.e., that comprises the amino acid sequence of the 51 amino acid human insulin sequence, or equivalent functional variants thereof) that is suitable for enteral administration. In particular examples, the insulin is purified from a natural source (isolated tissue). In other examples, the insulin is purified recombinant insulin. In still other examples, the insulin is purified synthetic insulin. In still other examples, the insulin is a mixture of one or more of natural isolated, recombinant, or synthetic. It will be understood that insulin for use in the described compositions and methods is commercially available from multiple pharmaceutical suppliers including, but not limited to, Eli Lilly and Co (Indianapolis, Ind.), Novo Nordisk A/S (Denmark), and Sanofi US (Bridgewater, N.J.).

Any method as is known in the art for oral delivery of a compound to an infant can be used according to the teachings of the present invention. According to certain embodiments, insulin is administered within a semi-solid insulin-enriched infant formula. According to other embodiments, insulin is administered as liquid insulin-enriched infant formula. According to some embodiments, the infant formula is administered at an average daily feeding volume similar to that of breastfed infants during the initial weeks or months of life.

Calculations of the optimal formula quantities to be administered to newborn to 6 months old infants are based on energy and protein consumption as observed in healthy infants receiving breast milk as the sole nutrition. Assuming energy content of the formula to be 60-75 kcal/100 ml (according to the minimum permitted protein content in the EU) recommended formula consumption is between 115 to 215 ml/Kg/day (Report of the Scientific Committee on Food on the Revision of Essential Requirements of Infant Formulae and Follow-on Formulae, May 2003).

According to certain embodiments, the insulin is encapsulated within encapsulating material providing stability to the insulin. As used herein, the term "insulin stability" refers to maintaining at least 60%, 70%, 80%, 85%, 90% 95% or 100% of the insulin initial activity. Methods of encapsulating insulin are known in the art. Examples of such methods are provided in International Patent Applications Publication Nos. WO 2004/112494 and WO 2005/115473, assigned to the Applicant of the present invention.

In the food and pharmaceutical industries, for example, microencapsulation is used to stabilize the core material, to control the timing and rate of the release of the core material and to separate and prevent chemical interaction between reactive or incompatible components of a multicomponent formulation. Thus, microencapsulation makes it possible to protect sensitive bioactive agents, to ensure against activity loss and to mask or preserve flavors and aromas. Encapsulation may be used to preserve biological activity of bioactive ingredient, such as growth promoting agents against any of the following or similarly destructive factors: adverse temperature, pressure, humidity, pH, osmotic concentration, ionic concentration, chemical degradation, presence of metals, surfactants and chelators, radiation (including but not limited to UV, IR, visible light), enzymatic and microbial degradation and combinations thereof.

Release of the encapsulated bioactive ingredient may occur spontaneously in the digestive tract, or may be the result of environmental events.

According to certain embodiments, a protective layer surrounding or incorporating the insulin is specifically designed to degrade, or undergo controlled release as a response to exposure to the change in environmental condition. The change in the environmental condition can be time, temperature, moisture content, pressure, or pH, ionic strength, enzymatic activity, or a combination thereof. According to other embodiments, the insulin is encapsulated in a material designed to protect it from digestion in the digestive system of the infant and to release the insulin only as a response to an increase in pH. The insulin may be further encapsulated with another encapsulating material, designed to protect the core from increased temperature. The skilled artisan in the art, would recognize that the order of environmental triggers releasing the active compound is not rigid and depends on the environmental conditions of manufacturing, environmental conditions of integration into food products, environmental conditions of storage after integration onto food products, desired delivery location within the gastrointestinal system, timing and physiological activity desired.

Any factor that may affect the entrapment of insulin in a biodegradable matrix and thereby affect its initial loading, subsequent release, or a combination thereof, may be utilized. Such factors may comprise inter-alia, the initial solvent concentration, its molecular size and polarity, the temperature and pressure under which the solvent is removed, molecular weight number (MWn) average of the biodegradable matrix, and its polydispersity index. When the biodegradable matrix is a polymer, the size and polarity of the insulin, the monomer ratio and distribution along the copolymer's chain, or a combination thereof may be also considered. In addition, D/L ratio within each monomer of a biodegradable polymer will affect release rates. The term D/L ratio refers to the ratio of monomer molecules that affect the direction (D-right, L-left), in which a cross-polarized lens will be rotated when observing a single optically active monomer like lactic acid. Since most mammals have D-specific enzymes, that ratio will affect the digestion rate of the biodegradable biopolymer, affecting its molecular weight and consequently its viscosity, thereby affecting release rate of the entrapped insulin.

Various materials may be used as the encapsulated material as described, for example, in WO 2004/112494 and WO 2005/115473 cited above. According to certain currently preferred embodiments, insulin is microencapsulated within a matrix of maltodextrin (MD) and vitamin C as described in WO 2005/115473.

The encapsulated insulin can be mixed with any infant formula as is known in the art. The encapsulation can also protect the insulin in a manner that, when a liquid formula containing the encapsulated insulin in consumed by an SGA infant, the insulin is protected, at least partially, during its passage through the newborn gastrointestinal track or stomach such that sufficient amount of insulin is still active to exert its growth-enhancing activity as described herein.

Kits

In particular embodiments, the insulin-supplemented IF described herein is provided in a kit. In particular examples, the kits contain IF either pre-mixed with insulin at defined concentrations. In other examples, the insulin is provided separately from the IF. Kits of the present disclosure contain instructions for providing IF containing defined insulin concentrations at particular postnatal days, and at particular times of day, such that the concentration of insulin provided at the indicated day mimics the insulin concentration in HM at the given postpartum day in the morning, afternoon, and evening, for example as indicated in Table 1.

In some examples, the kit includes insulin-supplemented IF having a single insulin concentration to mimic the natural insulin component in HM at a particular post-partum time point. In other examples, the described kits can include multiple IF portions, each with a different insulin concentration in order to mimic the natural insulin component in HM at multiple postpartum time points. In some embodiments, the kits provide the IF in a liquid ready-to-feed (RTF) formula. In other embodiments the RTF IF is supplemented with insulin at 10-15 µU/ml, and can be used to mimic the natural insulin component of HM in the afternoon (12 PM-6 PM) at day 1 postpartum. In other embodiments the RTF IF is supplemented with insulin at 8-12 µU/ml, and can be used to mimic the natural insulin component of HM in the morning (6 AM-12 PM) at day 4 postpartum. In still other embodiments, the RTF IF is supplemented with insulin at 8-11 µU/ml, and can be used to mimic the natural insulin component of HM in the evening (6 PM-12 AM) at day 29 postpartum.

In still other examples, the kits provide insulin-supplemented IF that is packaged in a matrix of between 2 and 24 daily portions, such as 3 daily portions, for any number of days such as 7 days, 14 days, 21 days, 28 days, 35 days, 42 days, 49 days, 56 days, 63 days, 70 days, 77 days, 84 days, 91 days, or longer. In example where 3 portions are provided for a particular day, the added insulin for each portion corresponds to the insulin concentration in human milk in the morning, afternoon, and evening for the specific day. In an alternative example, where 2 portions are provided for a particular day, the added insulin for each portion corresponds to the insulin average concentration in human milk in the morning and afternoon (6 AM to 6 PM) and in the evening-early night (6 PM to 12:00 PM) for the specific day.

In certain embodiments, the described kits include IF supplemented with insulin at a concentration to mimic the average concentration of insulin in HM after postpartum day 30. According to some embodiments, the concentration of insulin in HM after postpartum day 30 reached a plateau.

Methods of Feeding Infants with Insulin-Supplemented Formula

Additionally described herein are methods of feeding an infant with the disclosed IF so that the concentration of insulin provided mimics that found in HM at the postpartum time of feeding. According to some embodiments, the insulin concentration at a certain day and time of day postpartum is shown in Table 1. Current IF formulations lack an insulin component that corresponds to the actual insulin concentrations of HM on a given postpartum day and/or at a given time of the day.

Among the benefits of the described methods is the ability to interchange IF and HM feeding to an infant while maintaining a similar insulin exposure throughout. Accordingly, in particular examples, an infant is fed with HM for a portion of a day, and insulin-supplemented IF for other portions of a day.

In some embodiments, the infant to be fed is a preterm newborn. In such methods the insulin added to the IF is intended to match the insulin in HM of a preterm infant mother until the preterm infant reaches full-term age. Postpartum diabetic mothers (type I and type II diabetes) produce HM with abnormal insulin concentrations. In other embodiments, the mother of the infant to be fed is diabetic, and the methods provide insulin-supplemented IF to the infant at normal insulin concentrations.

In certain examples the insulin-supplemented IF is provided as a drug product. In other currently typical examples, the insulin-supplemented IF is provided as a medical food product. In other examples, the insulin-supplemented IF is provided as a nutritional food supplement. In still further examples, the insulin-supplemented-IF is provided as a dietary supplement, and/or a classification of infant formula.

In particular embodiments, the described methods provide for feeding an infant with IF supplemented with insulin corresponding to a natural insulin concentration in HM from the time of birth up to 3 days postpartum, up to 7 days postpartum, up to 10 days postpartum, up to 14 days postpartum, up to 21 days postpartum, up to 28 days postpartum, up to 35 days postpartum, up to 42 days postpartum, up to 49 days postpartum, up to 56 days postpartum, up to 63 days postpartum, up to 70 days postpartum, up to 77 days postpartum, up to 84 days postpartum, up to 90 days postpartum, or beyond 90 days postpartum.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1

Insulin Concentrations in Milk of Postpartum Women

This example describes the measurement of insulin in the milk of postpartum women.

Figure 2:
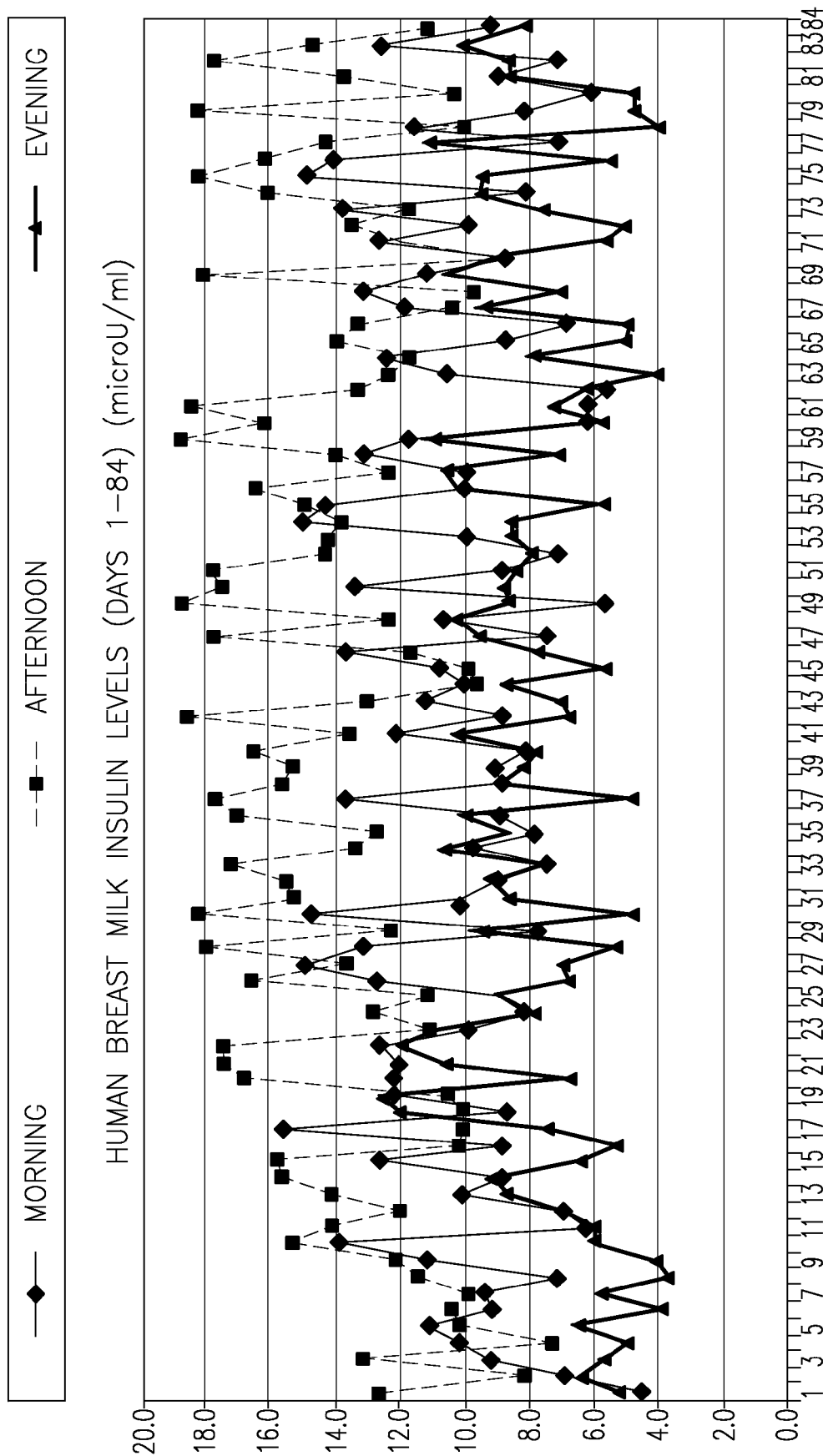
FIG. 2 shows the average insulin concentration in HM from day 1 to day 84 postpartum as separate plots for morning (6 AM-12 PM), afternoon (12 PM-6 PM); and evening (6 PM-12 AM).
Figure 3A:
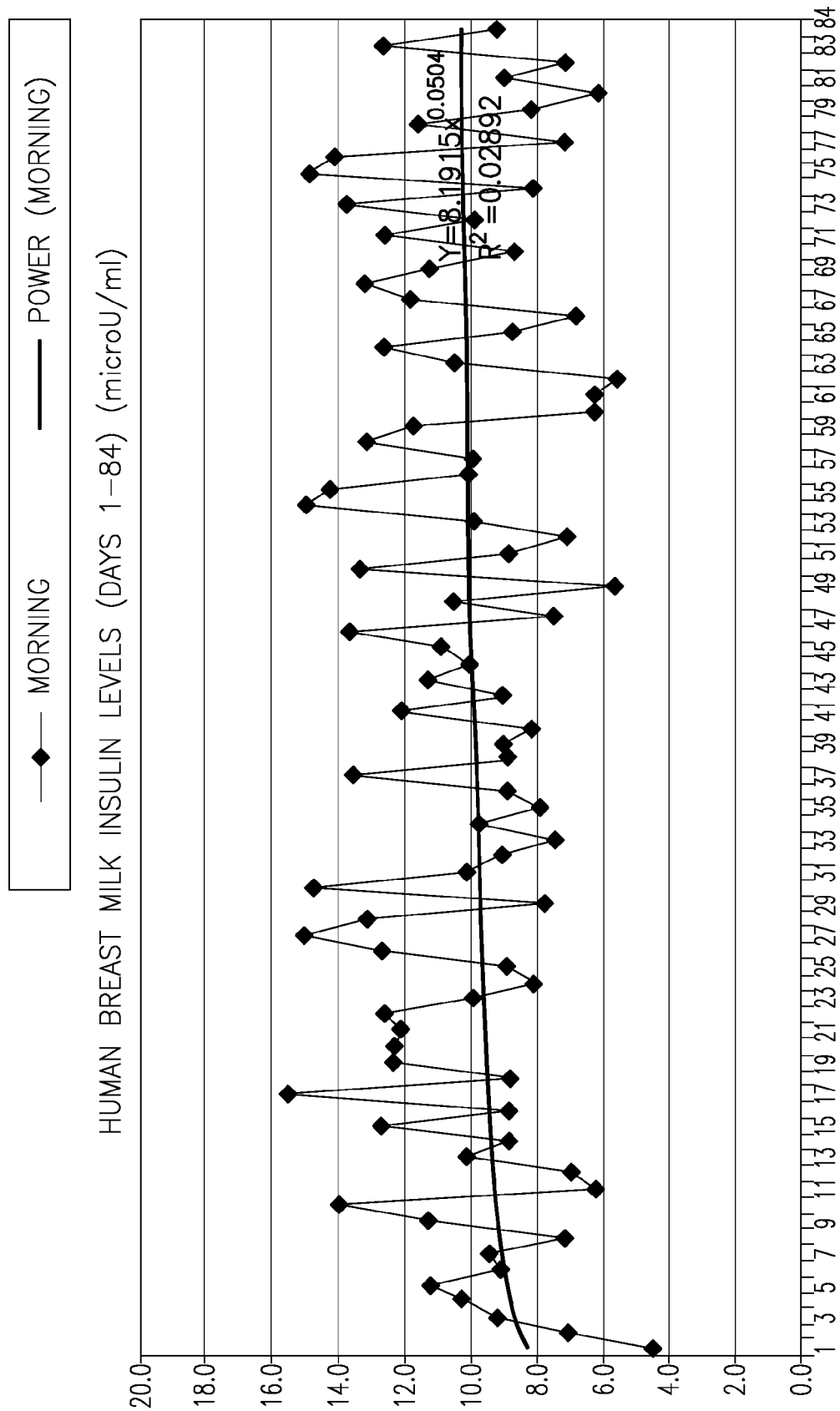
FIG. 3A-3C show the average insulin concentration in HM from day 1 to day 84 postpartum.
Figure 3B:
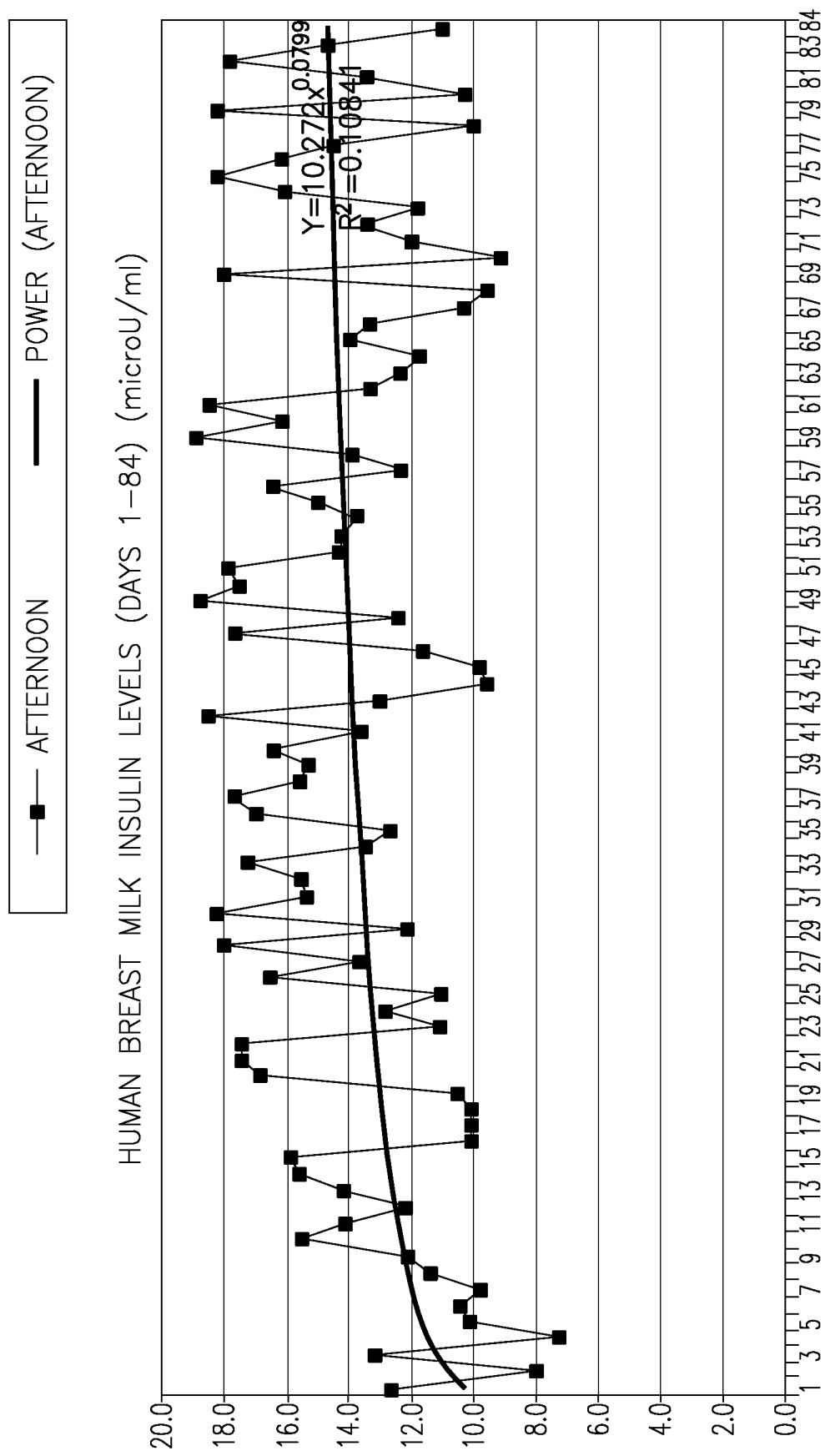
Figure 3C:
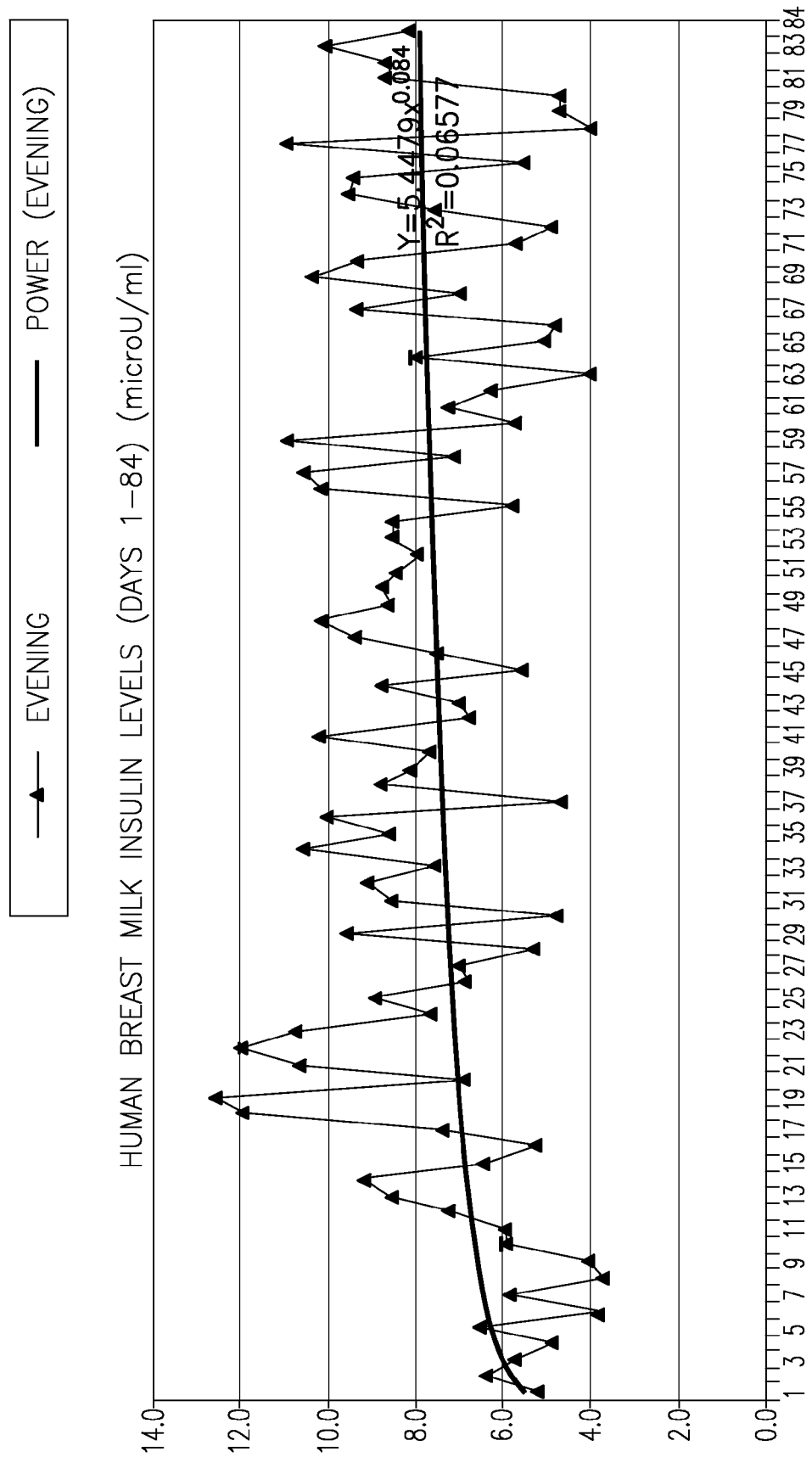

The insulin concentration in milk produced by 30 women was collected three times a day (morning (6 AM-12 PM), afternoon (12 PM-6 PM) and evening (6 PM-12 AM), up to postpartum day 84. The insulin concentration in each sample of milk was then determined. Table 1 shows the results of this survey. Insulin concentrations are in µ/ml of milk. The following data is also presented in FIGS. 1-3 as plots with accompanying trend lines. FIG. 2 clearly shows the diurnal fluctuation of the insulin concentrations in human milk.

Figure 4:
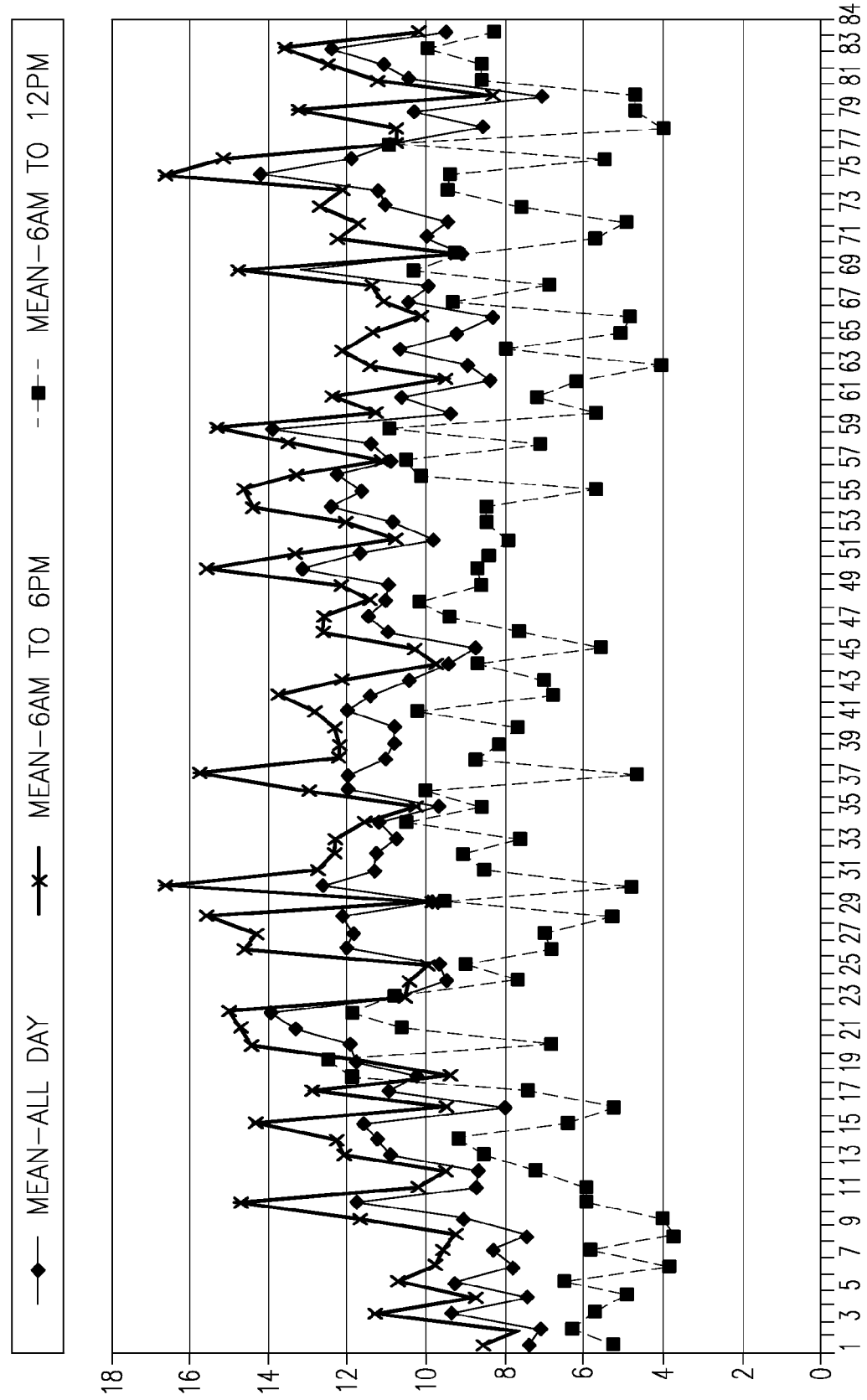
FIG. 4 shows the average insulin concentration in HM in samples taken in the morning and afternoon combined, and in the evening, from day 1 to day 84 postpartum.

Based on data presented in Table 1, and in order to ease the feeding of the insulin supplemented formula, the insulin concentration in the formula can be determined according to the mean of insulin concentration in HM at different intervals of a given day or in joint intervals of a given day postpartum. In this example the day period of time is divided into two parts: the first part encompasses insulin values in the morning and afternoon (6 AM-6 PM) and the second part encompasses the evening (6 PM-12 AM), until day 84 postpartum. The data are presented in Table 2 and further in FIG. 4 as plots. It is well appreciated that insulin supplemented infant formulae of the present invention can mimic the insulin concentration of human milk at the level of day 30 postpartum and after, and/or day 84 postpartum and after, and as long as infant formula feeding is needed.

In other example, and in order to ease feeding of the insulin supplemented formula, the final concentration of insulin in the formula for administering during the morning and afternoon period (6 AM-6 PM) is up to 10% higher than the average of insulin concentration measured in human milk during the morning and afternoon period, and up to 10% lower in the formula for administering at the evening (6 PM-12 AM or 6 PM-6 AM) than the average concentration of insulin measured in the human milk during the evening, The insulin concentrations in the milk samples of the present study presented in Tables 1 and 2 hereinbelow are at the lower end of the insulin concentration previously reported (Shehadeh N. et al., 2001, ibid). Without wishing to be bound by any specific theory or mechanism of action, the lower levels obtained may be a result of the detection (ELISA) method used. It is to be appreciated that the insulin concentration may be measured by any method as is known to a person skilled in the art. In preferred embodiments, the insulin concentration in the human milk is measured by its biological activity, and the insulin concentration in the formula portions provided in the kits and methods of the invention is determined accordingly.

TABLE 1

Insulin concentration in HM measured in the morning, noon and evening

| DAY | Time point | Mean Insulin | Range Low | Range High |
|---|---|---|---|---|
| Day 1 | Morning | 4.4 | 3.5 | 5.3 |
| Day 1 | Afternoon | 12.6 | 10.1 | 15.1 |
| Day 1 | Evening | 5.2 | 4.2 | 6.2 |
| Day 2 | Morning | 7 | 5.6 | 8.4 |
| Day 2 | Afternoon | 8.1 | 6.5 | 9.7 |
| Day 2 | Evening | 6.3 | 5 | 7.6 |
| Day 3 | Morning | 9.1 | 7.3 | 10.9 |
| Day 3 | Afternoon | 13.1 | 10.5 | 15.7 |
| Day 3 | Evening | 5.7 | 4.6 | 6.8 |
| Day 4 | Morning | 10.1 | 8.1 | 12.1 |
| Day 4 | Afternoon | 7.3 | 5.8 | 8.8 |
| Day 4 | Evening | 4.9 | 3.9 | 5.9 |
| Day 5 | Morning | 11.1 | 8.9 | 13.3 |
| Day 5 | Afternoon | 10.1 | 8.1 | 12.1 |
| Day 5 | Evening | 6.5 | 5.2 | 7.8 |
| Day 6 | Morning | 9.1 | 7.3 | 10.9 |
| Day 6 | Afternoon | 10.4 | 8.3 | 12.5 |
| Day 6 | Evening | 3.8 | 3 | 4.6 |
| Day 7 | Morning | 9.3 | 7.4 | 11.2 |
| Day 7 | Afternoon | 9.8 | 7.8 | 11.8 |
| Day 7 | Evening | 5.8 | 4.6 | 7 |
| Day 8 | Morning | 7.1 | 5.7 | 8.5 |
| Day 8 | Afternoon | 11.4 | 9.1 | 13.7 |
| Day 8 | Evening | 3.7 | 3 | 4.4 |
| Day 9 | Morning | 11.1 | 8.9 | 13.3 |
| Day 9 | Afternoon | 12.1 | 9.7 | 14.5 |
| Day 9 | Evening | 4 | 3.2 | 4.8 |
| Day 10 | Morning | 13.8 | 11 | 16.6 |
| Day 10 | Afternoon | 15.4 | 12.3 | 18.5 |
| Day 10 | Evening | 5.9 | 4.7 | 7.1 |
| Day 11 | Morning | 6.2 | 5 | 7.4 |
| Day 11 | Afternoon | 14.1 | 11.3 | 16.9 |
| Day 11 | Evening | 5.9 | 4.7 | 7.1 |
| Day 12 | Morning | 6.9 | 5.5 | 8.3 |
| Day 12 | Afternoon | 12 | 9.6 | 14.4 |
| Day 12 | Evening | 7.2 | 5.8 | 8.6 |
| Day 13 | Morning | 10 | 8 | 12 |
| Day 13 | Afternoon | 14.1 | 11.3 | 16.9 |
| Day 13 | Evening | 8.6 | 6.9 | 10.3 |
| Day 14 | Morning | 8.9 | 7.1 | 10.7 |
| Day 14 | Afternoon | 15.6 | 12.5 | 18.7 |
| Day 14 | Evening | 9.2 | 7.4 | 11 |
| Day 15 | Morning | 12.6 | 10.1 | 15.1 |
| Day 15 | Afternoon | 15.8 | 12.6 | 19 |
| Day 15 | Evening | 6.4 | 5.1 | 7.7 |
| Day 16 | Morning | 8.8 | 7 | 10.6 |
| Day 16 | Afternoon | 10.1 | 8.1 | 12.1 |
| Day 16 | Evening | 5.2 | 4.2 | 6.2 |
| Day 17 | Morning | 15.5 | 12.4 | 18.6 |
| Day 17 | Afternoon | 10 | 8 | 12 |
| Day 17 | Evening | 7.4 | 5.9 | 8.9 |
| Day 18 | Morning | 8.7 | 7 | 10.4 |
| Day 18 | Afternoon | 10 | 8 | 12 |
| Day 18 | Evening | 11.9 | 9.5 | 14.3 |
| Day 19 | Morning | 12.3 | 9.8 | 14.8 |
| Day 19 | Afternoon | 10.5 | 8.4 | 12.6 |
| Day 19 | Evening | 12.5 | 10 | 15 |
| Day 20 | Morning | 12.2 | 9.8 | 14.6 |
| Day 20 | Afternoon | 16.8 | 13.4 | 20.2 |
| Day 20 | Evening | 6.8 | 5.4 | 8.2 |
| Day 21 | Morning | 12 | 9.6 | 14.4 |
| Day 21 | Afternoon | 17.4 | 13.9 | 20.9 |
| Day 21 | Evening | 10.6 | 8.5 | 12.7 |
| Day 22 | Morning | 12.5 | 10 | 15 |
| Day 22 | Afternoon | 17.4 | 13.9 | 20.9 |
| Day 22 | Evening | 11.9 | 9.5 | 14.3 |
| Day 23 | Morning | 9.9 | 7.9 | 11.9 |
| Day 23 | Afternoon | 11.1 | 8.9 | 13.3 |
| Day 23 | Evening | 10.8 | 8.6 | 13 |
| Day 24 | Morning | 8 | 6.4 | 9.6 |
| Day 24 | Afternoon | 12.8 | 10.2 | 15.4 |
| Day 24 | Evening | 7.7 | 6.2 | 9.2 |
| Day 25 | Morning | 8.9 | 7.1 | 10.7 |
| Day 25 | Afternoon | 11 | 8.8 | 13.2 |
| Day 25 | Evening | 9 | 7.2 | 10.8 |
| Day 26 | Morning | 12.6 | 10.1 | 15.1 |
| Day 26 | Afternoon | 16.5 | 13.2 | 19.8 |

TABLE 1-continued

Insulin concentration in HM measured in the morning, noon and evening

| DAY | Time point | Mean Insulin | Range Low | Range High |
|---|---|---|---|---|
| Day 26 | Evening | 6.8 | 5.4 | 8.2 |
| Day 27 | Morning | 14.9 | 11.9 | 17.9 |
| Day 27 | Afternoon | 13.7 | 11 | 16.4 |
| Day 27 | Evening | 7 | 5.6 | 8.4 |
| Day 28 | Morning | 13.1 | 10.5 | 15.7 |
| Day 28 | Afternoon | 17.9 | 14.3 | 21.5 |
| Day 28 | Evening | 5.3 | 4.2 | 6.4 |
| Day 29 | Morning | 7.7 | 6.2 | 9.2 |
| Day 29 | Afternoon | 12.2 | 9.8 | 14.6 |
| Day 29 | Evening | 9.5 | 7.6 | 11.4 |
| Day 30 | Morning | 14.7 | 11.8 | 17.6 |
| Day 30 | Afternoon | 18.2 | 14.6 | 21.8 |
| Day 30 | Evening | 4.8 | 3.8 | 5.8 |
| Day 31 | Morning | 10.1 | 8.1 | 12.1 |
| Day 31 | Afternoon | 15.3 | 12.2 | 18.4 |
| Day 31 | Evening | 8.5 | 6.8 | 10.2 |
| Day 32 | Morning | 9.1 | 7.3 | 10.9 |
| Day 32 | Afternoon | 15.5 | 12.4 | 18.6 |
| Day 32 | Evening | 9.1 | 7.3 | 10.9 |
| Day 33 | Morning | 7.4 | 5.9 | 8.9 |
| Day 33 | Afternoon | 17.2 | 13.8 | 20.6 |
| Day 33 | Evening | 7.6 | 6.1 | 9.1 |
| Day 34 | Morning | 9.7 | 7.8 | 11.6 |
| Day 34 | Afternoon | 13.4 | 10.7 | 16.1 |
| Day 34 | Evening | 10.5 | 8.4 | 12.6 |
| Day 35 | Morning | 7.8 | 6.2 | 9.4 |
| Day 35 | Afternoon | 12.7 | 10.2 | 15.2 |
| Day 35 | Evening | 8.6 | 6.9 | 10.3 |
| Day 36 | Morning | 8.9 | 7.1 | 10.7 |
| Day 36 | Afternoon | 17 | 13.6 | 20.4 |
| Day 36 | Evening | 10 | 8 | 12 |
| Day 37 | Morning | 13.6 | 10.9 | 16.3 |
| Day 37 | Afternoon | 17.7 | 14.2 | 21.2 |
| Day 37 | Evening | 4.7 | 3.8 | 5.6 |
| Day 38 | Morning | 8.8 | 7 | 10.6 |
| Day 38 | Afternoon | 15.6 | 12.5 | 18.7 |
| Day 38 | Evening | 8.7 | 7 | 10.4 |
| Day 39 | Morning | 9 | 7.2 | 10.8 |
| Day 39 | Afternoon | 15.3 | 12.2 | 18.4 |
| Day 39 | Evening | 8.1 | 6.5 | 9.7 |
| Day 40 | Morning | 8.1 | 6.5 | 9.7 |
| Day 40 | Afternoon | 16.5 | 13.2 | 19.8 |
| Day 40 | Evening | 7.7 | 6.2 | 9.2 |
| Day 41 | Morning | 12.1 | 9.7 | 14.5 |
| Day 41 | Afternoon | 13.5 | 10.8 | 16.2 |
| Day 41 | Evening | 10.2 | 8.2 | 12.2 |
| Day 42 | Morning | 8.9 | 7.1 | 10.7 |
| Day 42 | Afternoon | 18.5 | 14.8 | 22.2 |
| Day 42 | Evening | 6.8 | 5.4 | 8.2 |
| Day 43 | Morning | 11.3 | 9 | 13.6 |
| Day 43 | Afternoon | 12.9 | 10.3 | 15.5 |
| Day 43 | Evening | 7 | 5.6 | 8.4 |
| Day 44 | Morning | 10 | 8 | 12 |
| Day 44 | Afternoon | 9.6 | 7.7 | 11.5 |
| Day 44 | Evening | 8.7 | 7 | 10.4 |
| Day 45 | Morning | 10.8 | 8.6 | 13 |
| Day 45 | Afternoon | 9.8 | 7.8 | 11.8 |
| Day 45 | Evening | 5.6 | 4.5 | 6.7 |
| Day 46 | Morning | 13.6 | 10.9 | 16.3 |
| Day 46 | Afternoon | 11.6 | 9.3 | 13.9 |
| Day 46 | Evening | 7.6 | 6.1 | 9.1 |
| Day 47 | Morning | 7.4 | 5.9 | 8.9 |
| Day 47 | Afternoon | 17.7 | 14.2 | 21.2 |
| Day 47 | Evening | 9.4 | 7.5 | 11.3 |
| Day 48 | Morning | 10.5 | 8.4 | 12.6 |
| Day 48 | Afternoon | 12.4 | 9.9 | 14.9 |
| Day 48 | Evening | 10.2 | 8.2 | 12.2 |
| Day 49 | Morning | 5.6 | 4.5 | 6.7 |
| Day 49 | Afternoon | 18.7 | 15 | 22.4 |
| Day 49 | Evening | 8.6 | 6.9 | 10.3 |
| Day 50 | Morning | 13.3 | 10.6 | 16 |
| Day 50 | Afternoon | 17.5 | 14 | 21 |
| Day 50 | Evening | 8.7 | 7 | 10.4 |
| Day 51 | Morning | 8.8 | 7 | 10.6 |
| Day 51 | Afternoon | 17.8 | 14.2 | 21.4 |
| Day 51 | Evening | 8.4 | 6.7 | 10.1 |
| Day 52 | Morning | 7.1 | 5.7 | 8.5 |
| Day 52 | Afternoon | 14.3 | 11.4 | 17.2 |
| Day 52 | Evening | 7.9 | 6.3 | 9.5 |
| Day 53 | Morning | 9.9 | 7.9 | 11.9 |
| Day 53 | Afternoon | 14.2 | 11.4 | 17 |
| Day 53 | Evening | 8.5 | 6.8 | 10.2 |
| Day 54 | Morning | 14.9 | 11.9 | 17.9 |
| Day 54 | Afternoon | 13.8 | 11 | 16.6 |
| Day 54 | Evening | 8.5 | 6.8 | 10.2 |
| Day 55 | Morning | 14.3 | 11.4 | 17.2 |
| Day 55 | Afternoon | 14.9 | 11.9 | 17.9 |
| Day 55 | Evening | 5.7 | 4.6 | 6.8 |
| Day 56 | Morning | 10 | 8 | 12 |
| Day 56 | Afternoon | 16.5 | 13.2 | 19.8 |
| Day 56 | Evening | 10.2 | 8.2 | 12.2 |
| Day 57 | Morning | 9.9 | 7.9 | 11.9 |
| Day 57 | Afternoon | 12.3 | 9.8 | 14.8 |
| Day 57 | Evening | 10.5 | 8.4 | 12.6 |
| Day 58 | Morning | 13.1 | 10.5 | 15.7 |
| Day 58 | Afternoon | 13.9 | 11.1 | 16.7 |
| Day 58 | Evening | 7.1 | 5.7 | 8.5 |
| Day 59 | Morning | 11.7 | 9.4 | 14 |
| Day 59 | Afternoon | 18.8 | 15 | 22.6 |
| Day 59 | Evening | 10.9 | 8.7 | 13.1 |
| Day 60 | Morning | 6.2 | 5 | 7.4 |
| Day 60 | Afternoon | 16.2 | 13 | 19.4 |
| Day 60 | Evening | 5.7 | 4.6 | 6.8 |
| Day 61 | Morning | 6.2 | 5 | 7.4 |
| Day 61 | Afternoon | 18.4 | 14.7 | 22.1 |
| Day 61 | Evening | 7.2 | 5.8 | 8.6 |
| Day 62 | Morning | 5.6 | 4.5 | 6.7 |
| Day 62 | Afternoon | 13.3 | 10.6 | 16 |
| Day 62 | Evening | 6.2 | 5 | 7.4 |
| Day 63 | Morning | 10.5 | 8.4 | 12.6 |
| Day 63 | Afternoon | 12.3 | 9.8 | 14.8 |
| Day 63 | Evening | 4 | 3.2 | 4.8 |
| Day 64 | Morning | 12.5 | 10 | 15 |
| Day 64 | Afternoon | 11.7 | 9.4 | 14 |
| Day 64 | Evening | 7.9 | 6.3 | 9.5 |
| Day 65 | Morning | 8.7 | 7 | 10.4 |
| Day 65 | Afternoon | 13.9 | 11.1 | 16.7 |
| Day 65 | Evening | 5 | 4 | 6 |
| Day 66 | Morning | 6.8 | 5.4 | 8.2 |
| Day 66 | Afternoon | 13.3 | 10.6 | 16 |
| Day 66 | Evening | 4.8 | 3.8 | 5.8 |
| Day 67 | Morning | 11.8 | 9.4 | 14.2 |
| Day 67 | Afternoon | 10.3 | 8.2 | 12.4 |
| Day 67 | Evening | 9.3 | 7.4 | 11.2 |
| Day 68 | Morning | 13.1 | 10.5 | 15.7 |
| Day 68 | Afternoon | 9.6 | 7.7 | 11.5 |
| Day 68 | Evening | 6.9 | 5.5 | 8.3 |
| Day 69 | Morning | 11.1 | 8.9 | 13.3 |
| Day 69 | Afternoon | 18 | 14.4 | 21.6 |
| Day 69 | Evening | 10.3 | 8.2 | 12.4 |
| Day 70 | Morning | 8.7 | 7 | 10.4 |
| Day 70 | Afternoon | 9 | 7.2 | 10.8 |
| Day 70 | Evening | 9.2 | 7.4 | 11 |
| Day 71 | Morning | 12.5 | 10 | 15 |
| Day 71 | Afternoon | 11.9 | 9.5 | 14.3 |
| Day 71 | Evening | 5.7 | 4.6 | 6.8 |
| Day 72 | Morning | 9.9 | 7.9 | 11.9 |
| Day 72 | Afternoon | 13.5 | 10.8 | 16.2 |
| Day 72 | Evening | 4.9 | 3.9 | 5.9 |
| Day 73 | Morning | 13.7 | 11 | 16.4 |
| Day 73 | Afternoon | 11.7 | 9.4 | 14 |
| Day 73 | Evening | 7.6 | 6.1 | 9.1 |
| Day 74 | Morning | 8.1 | 6.5 | 9.7 |
| Day 74 | Afternoon | 16 | 12.8 | 19.2 |
| Day 74 | Evening | 9.5 | 7.6 | 11.4 |
| Day 75 | Morning | 14.9 | 11.9 | 17.9 |
| Day 75 | Afternoon | 18.2 | 14.6 | 21.8 |
| Day 75 | Evening | 9.4 | 7.5 | 11.3 |

TABLE 1-continued

Insulin concentration in HM measured in the morning, noon and evening

| DAY | Time point | Mean Insulin | Range Low | Range High |
|---|---|---|---|---|
| Day 76 | Morning | 14 | 11.2 | 16.8 |
| Day 76 | Afternoon | 16.2 | 13 | 19.4 |
| Day 76 | Evening | 5.5 | 4.4 | 6.6 |
| Day 77 | Morning | 7.1 | 5.7 | 8.5 |
| Day 77 | Afternoon | 14.3 | 11.4 | 17.2 |
| Day 77 | Evening | 10.9 | 8.7 | 13.1 |
| Day 78 | Morning | 11.5 | 9.2 | 13.8 |
| Day 78 | Afternoon | 10 | 8 | 12 |
| Day 78 | Evening | 4 | 3.2 | 4.8 |
| Day 79 | Morning | 8.1 | 6.5 | 9.7 |
| Day 79 | Afternoon | 18.2 | 14.6 | 21.8 |
| Day 79 | Evening | 4.7 | 3.8 | 5.6 |
| Day 80 | Morning | 6.1 | 4.9 | 7.3 |
| Day 80 | Afternoon | 10.3 | 8.2 | 12.4 |
| Day 80 | Evening | 4.7 | 3.8 | 5.6 |
| Day 81 | Morning | 8.9 | 7.1 | 10.7 |
| Day 81 | Afternoon | 13.6 | 10.9 | 16.3 |
| Day 81 | Evening | 8.6 | 6.9 | 10.3 |
| Day 82 | Morning | 7.1 | 5.7 | 8.5 |
| Day 82 | Afternoon | 17.7 | 14.2 | 21.2 |
| Day 82 | Evening | 8.6 | 6.9 | 10.3 |
| Day 83 | Morning | 12.5 | 10 | 15 |
| Day 83 | Afternoon | 14.7 | 11.8 | 17.6 |
| Day 83 | Evening | 10 | 8 | 12 |
| Day 84 | Morning | 9.2 | 7.4 | 11 |
| Day 84 | Afternoon | 11.1 | 8.9 | 13.3 |
| Day 84 | Evening | 8.2 | 6.6 | 9.8 |

TABLE 2

Mean Insulin concentration in HM, at different time intervals

| Day | Mean—all day | Mean—6 AM to 6 PM | Mean—6 PM to 12 PM |
|---|---|---|---|
| 1 | 7.4 | 8.5 | 5.2 |
| 2 | 7.1 | 7.6 | 6.3 |
| 3 | 9.3 | 11.1 | 5.7 |
| 4 | 7.4 | 8.7 | 4.9 |
| 5 | 9.2 | 10.6 | 6.5 |
| 6 | 7.8 | 9.8 | 3.8 |
| 7 | 8.3 | 9.6 | 5.8 |
| 8 | 7.4 | 9.3 | 3.7 |
| 9 | 9.1 | 11.6 | 4.0 |
| 10 | 11.7 | 14.6 | 5.9 |
| 11 | 8.7 | 10.2 | 5.9 |
| 12 | 8.7 | 9.5 | 7.2 |
| 13 | 10.9 | 12.1 | 8.6 |
| 14 | 11.2 | 12.3 | 9.2 |
| 15 | 11.6 | 14.2 | 6.4 |
| 16 | 8.0 | 9.5 | 5.2 |
| 17 | 11.0 | 12.8 | 7.4 |
| 18 | 10.2 | 9.4 | 11.9 |
| 19 | 11.8 | 11.4 | 12.5 |
| 20 | 11.9 | 14.5 | 6.8 |
| 21 | 13.3 | 14.7 | 10.6 |
| 22 | 13.9 | 15.0 | 11.9 |
| 23 | 10.6 | 10.5 | 10.8 |
| 24 | 9.5 | 10.4 | 7.7 |
| 25 | 9.6 | 10.0 | 9.0 |
| 26 | 12.0 | 14.6 | 6.8 |
| 27 | 11.9 | 14.3 | 7.0 |
| 28 | 12.1 | 15.5 | 5.3 |
| 29 | 9.8 | 10.0 | 9.5 |
| 30 | 12.6 | 16.5 | 4.8 |
| 31 | 11.3 | 12.7 | 8.5 |
| 32 | 11.2 | 12.3 | 9.1 |
| 33 | 10.7 | 12.3 | 7.6 |
| 34 | 11.2 | 11.6 | 10.5 |
| 35 | 9.7 | 10.3 | 8.6 |
| 36 | 12.0 | 13.0 | 10.0 |
| 37 | 12.0 | 15.7 | 4.7 |
| 38 | 11.0 | 12.2 | 8.7 |
| 39 | 10.8 | 12.2 | 8.1 |
| 40 | 10.8 | 12.3 | 7.7 |
| 41 | 11.9 | 12.8 | 10.2 |
| 42 | 11.4 | 13.7 | 6.8 |
| 43 | 10.4 | 12.1 | 7.0 |
| 44 | 9.4 | 9.8 | 8.7 |
| 45 | 8.7 | 10.3 | 5.6 |
| 46 | 10.9 | 12.6 | 7.6 |
| 47 | 11.5 | 12.6 | 9.4 |
| 48 | 11.0 | 11.5 | 10.2 |
| 49 | 11.0 | 12.2 | 8.6 |
| 50 | 13.2 | 15.4 | 8.7 |
| 51 | 11.7 | 13.3 | 8.4 |
| 52 | 9.8 | 10.7 | 7.9 |
| 53 | 10.9 | 12.1 | 8.5 |
| 54 | 12.4 | 14.4 | 8.5 |
| 55 | 11.6 | 14.6 | 5.7 |
| 56 | 12.2 | 13.3 | 10.2 |
| 57 | 10.9 | 11.1 | 10.5 |
| 58 | 11.4 | 13.5 | 7.1 |
| 59 | 13.8 | 15.3 | 10.9 |
| 60 | 9.4 | 11.2 | 5.7 |
| 61 | 10.6 | 12.3 | 7.2 |
| 62 | 8.4 | 9.5 | 6.2 |
| 63 | 8.9 | 11.4 | 4.0 |
| 64 | 10.7 | 12.1 | 7.9 |
| 65 | 9.2 | 11.3 | 5.0 |
| 66 | 8.3 | 10.1 | 4.8 |
| 67 | 10.5 | 11.1 | 9.3 |
| 68 | 9.9 | 11.4 | 6.9 |
| 69 | 13.1 | 14.6 | 10.3 |
| 70 | 9.0 | 8.9 | 9.2 |
| 71 | 10.0 | 12.2 | 5.7 |
| 72 | 9.4 | 11.7 | 4.9 |
| 73 | 11.0 | 12.7 | 7.6 |
| 74 | 11.2 | 12.1 | 9.5 |
| 75 | 14.2 | 16.6 | 9.4 |
| 76 | 11.9 | 15.1 | 5.5 |
| 77 | 10.8 | 10.7 | 10.9 |
| 78 | 8.5 | 10.8 | 4.0 |
| 79 | 10.3 | 13.2 | 4.7 |
| 80 | 7.0 | 8.2 | 4.7 |
| 81 | 10.4 | 11.3 | 8.6 |
| 82 | 11.1 | 12.4 | 8.6 |
| 83 | 12.4 | 13.6 | 10.0 |
| 84 | 9.5 | 10.2 | 8.2 |

Example 2

A Kit for Providing Insulin-Supplemented IF

This example describes a kit providing IF supplemented with insulin, and which specifies the insulin concentration to be provided at a given postpartum day and a given time of day.

The kit contains individually-mixed RTF portions of insulin-supplemented IF. Each portion is labeled with the day or days and the time of day that the portion is to be fed to the infant in order to provide the natural insulin component in HM at the specified day and time of day. Myriad packaging configurations of the described kits are contemplated, including a single-portion kit with insulin-supplemented IF providing only a single insulin concentration, to a multiple-portion kit, which provides multiple portions with multiple insulin concentrations.

In one example, the described kit provides RTF IF with insulin concentrations suitable to mimic the natural insulin concentration in HM in the morning, afternoon, and evening of at least a single day. In a particular example, the kit provides insulin-supplemented IF for day 30 postpartum wherein the morning portion is supplemented with insulin at 15 μU/ml RTF IF, the afternoon portion is supplemented with insulin at 18 μU/ml RTF IF, and the evening portion is supplemented with insulin at 5 μU/ml RTF IF. Optionally, the kit contains instructions for providing the appropriate concentration of insulin to an infant at the appropriate day or days and time of day. In another example, the kit provides dry powdered IF or liquid (RTF or concentrated) IF and insulin in different containers (or in pre-measured individual containers), and instructions for how to mix IF with a particular insulin concentration such that the insulin concentration mimics the natural concentration found in HM at a given postpartum day and time of day as described in Table 1. According to certain typical examples, the insulin at a pre-determined concentration is provided in a sachet attached to the cover of a container containing the IF, such that the insulin is combined with the IF upon opening.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A kit for insulin-supplemented infant formula, comprising:
   a plurality of portions of infant formula, wherein each portion comprises insulin,
   wherein the concentration of the insulin in each of the plurality of portions mimics the concentration of insulin in human milk at a given day and time of day postpartum,
   wherein the day is between day 1 to day 84 postpartum,
   wherein the time of day is selected from 6 AM to 12 PM, 12 PM to 6 PM, 6 PM to 12 AM, 6 AM to 6 PM and 6 PM to 6 AM; and
   instructions for feeding an infant with the insulin-supplemented infant formula.

2. The kit of claim 1, wherein the concentration of insulin in each portion of formula corresponds to the concentration range of insulin indicated at a given day and time of day in Table 1.

3. The kit of claim 1, wherein the concentration of insulin in each portion of formula corresponds to the mean concentration of insulin indicated at a given day and time of day in Table 1.

4. The kit of claim 1, wherein the day is between day 1 to day 30 postpartum.

5. The kit of claim 1, wherein the day is between day 30 to day 84 postpartum.

6. The kit of claim 4, wherein the concentration of insulin in each portion of the formula is selected from (i) a concentration that is 10% higher than the mean concentration of the insulin measured between 6 AM to 6 PM at a given day postpartum and (ii) a concentration that is 10% lower than the average concentration of the insulin measured between 6 PM to 12 AM at a given day postpartum.

7. The kit of claim 4, wherein the concentration of insulin in each portion of formula is selected from (i) a concentration corresponding to the mean concentration of insulin indicated at a given day and time of day in Table 2 (ii) a concentration that is 10% higher than the mean concentration of the insulin measured between 6 AM to 6 PM at a given day in Table 2 and (ii) a concentration that is 10% lower than the average concentration of the insulin measured between 6 PM to 12 AM at a given day in Table 2.

8. The kit of claim 1, wherein the insulin is encapsulated in an encapsulating matrix.

9. The kit of claim 8, wherein the encapsulating matrix comprises encapsulating material selected from the group consisting of polysaccharide, milk powder, whey protein, lipid, gum Arabic, or microcrystalline cellulose.

10. The kit of claim 8, wherein the encapsulating material is maltodextrine, and wherein the matrix further comprises anti-oxidant.

11. The kit of claim 1, wherein the insulin is biologically active.

12. The kit of claim 1, wherein the insulin is mammalian insulin selected from the group consisting of human insulin and bovine insulin.

13. The kit of claim 1, wherein the formula is in a form selected from the group consisting of: dry powder for reconstitution with water, liquid concentrate for reconstitution with water and liquid ready-to-feed formula.

14. A kit for insulin-supplemented infant formula, comprising:
   a plurality of portions of infant formula;
   a plurality of portions of insulin; and
   instructions for how to mix the insulin with the formula such that the insulin concentration in the formula mimics the concentration of insulin in human milk at a given day and time of day postpartum,
   wherein the day is between day 1 to day 84 postpartum,
   wherein the time of day is selected from 6 AM to 12 PM, 12 PM to 6 PM, 6 PM to 12 AM, 6 AM to 6 PM and 6 PM to 6 AM.

15. The kit of claim 14, wherein the concentration of insulin in each portion of insulin corresponds to the concentration range of insulin indicated at a given day and time of day in Table 1.

16. The kit of claim 14, wherein the concentration of insulin in each portion of insulin corresponds to the mean concentration of insulin indicated at a given day and time of day in Table 1.

17. The kit of claim 14, wherein the insulin is encapsulated in an encapsulating matrix.

18. The kit of claim 14, wherein the insulin is biologically active.

19. The kit of claim 14, wherein the formula is in a form selected from the group consisting of: dry powder for reconstitution with water, liquid concentrate for reconstitution with water and liquid ready-to-feed formula.

20. A kit for insulin-supplemented infant formula, comprising a plurality of portions of infant formula, a plurality of portions of insulin; and instructions for how to mix the insulin with the formula such that the insulin concentration in the formula mimics the concentration of insulin in human milk at a given time period postpartum, wherein the time period postpartum is selected from day 0-5, 6-15, 16-30, 31-60, 61-90.

* * * * *